US00PP12332P2

(12) United States Plant Patent
Cascante

(10) Patent No.: US PP12,332 P2
(45) Date of Patent: Jan. 8, 2002

(54) DOUBLE IMPATIENS PLANT NAMED 'CAMEO SALMON CHIFFON'

(75) Inventor: Xenia Cascante, Alajuela (CR)

(73) Assignee: Oglevee Ltd., Connellsville, PA (US)

( * ) Notice: Subject to any disclaimer, the term of this patent is extended or adjusted under 35 U.S.C. 154(b) by 1 days.

(21) Appl. No.: 09/712,342

(22) Filed: Nov. 15, 2000

(51) Int. Cl.[7] ..... A01H 5/00
(52) U.S. Cl. ..... Plt./317

(58) Field of Search ..... Plt./317

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Double Impatiens plant named 'Cameo Salmon Chiffon', characterized by its large light and dark pink bi-colored flowers; fully double flower form; freely flowering habit with flowers positioned above the foliage; compact, mounded, spreading, densely foliated, and freely branching plant habit; rapid growth rate; and large rounded dark green leaves.

1 Drawing Sheet

BACKGROUND OF THE INVENTION

The present Invention relates to a new and distinct cultivar of Double Impatiens plant, botanically known as *Impatiens walleriana*, and hereinafter referred to by the cultivar name Cameo Salmon Chiffon.

The new Impatiens is a product of a planned breeding program conducted by the Inventor in Cartago, Costa Rica. The objective of the breeding program was to develop new compact Double Impatiens culitvars with large fully double flowers, excellent branching, and interesting flower and foliage colors.

The new Impatiens originated from a cross made by the Inventor of the Inventor's proprietary *Impatiens walleriana* selection code number W1, not patented, as the male, or pollen parent, with the Inventor's proprietary *Impatiens walleriana* selection code number 8713A, not patented, as the female, or seed parent. The cultivar Cameo Salmon Chiffon was discovered and selected by the Inventor as a flowering plant within the progeny of the stated cross in a controlled environment in Cartago, Costa Rica.

Asexual reproduction of the new cultivar by terminal cuttings taken at Cartago, Costa Rica, has shown that the unique features of this new Impatiens are stable and reproduced true to type in successive generations of asexual reproduction.

SUMMARY OF THE INVENTION

The following traits have been repeatedly observed and are determined to be the unique characteristics of 'Cameo Salmon Chiffon'. These characteristics in combination distinguish 'Cameo Salmon Chiffon' as a new and distinct cultivar:

1. Large light and dark pink bi-colored flowers.
2. Fully double flower form.
3. Freely flowering habit.
4. Flowers positioned above the foliage.
5. Compact, mounded and spreading plant habit.
6. Rapid growth rate.
7. Freely branching habit.
8. Large rounded dark green leaves; densely foliated.

In addition to flower color, plants of the new Impatiens differ from plants of the male parent, the selection W1, in the following characteristics:

1. Plants of the new Impatiens are more compact than and not as upright as plants of the selection W1.
2. Leaves of plants of the new Impatiens are larger and more rounded than leaves of plants of the selection W1.
3. Plants of the new Impatiens have larger flowers than plants of the selection W1.
4. Flowers of plants of the new Impatiens are fully double whereas flowers of plants of the selection W1 are semi-double.

In addition to flower color, plants of the new Impatiens differ from plants of the female parent, the selection 8713A, in the following characteristics:

1. Leaves of plants of the new Impatiens are larger and more rounded than leaves of plants of the selection 8713A.
2. Plants of the new Impatiens have larger flowers than plants of the selection 8713A.
3. Flowers of plants of the new Impatiens are fully double whereas flowers of plants of the selection 8713A are single.
4. Flowers of plants of the new Impatiens are sterile whereas flowers of plants of the selection 8713A are fertile.

The new Impatiens can be compared to the *Impatiens walleriana* cultivar Sparkler Salmon, disclosed in U.S. Plant Pat. No. 9,618. However, in side-by-side comparisons conducted in Lompoc, Calif., plants of the new Impatiens differ from plants of the cultivar Sparkler Salmon in the following characteristics:

1. Plants of the new Impatiens and plants of the cultivar Sparkler Salmon differ in flower colors; flower colors of plants of the new Impatiens are 55C and 52D whereas flower colors of plants of the cultivar Sparkler Salmon are 41C, 43D and 155C.
2. Flowers of plants of the new Impatiens are larger and have more petals than flowers of plants of the cultivar Sparkler Salmon.
3. Plants of the new Impatiens are more mounded and spreading than plants of the cultivar Sparkler Salmon which tend to be more upright in plant habit.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a top perspective view of typical handing basket container of 'Cameo Salmon Chiffon' with three plants per container. The age and the age and environmental conditions of the plant depicted in the photograph are the same as those described in the Detailed Botanical Description.

DETAILED BOTANICAL DESCRIPTION

The cultivar Cameo Salmon Chiffon has not been observed under all possible environmental conditions. The phenotype may vary somewhat with variations in environment such as temperature, light intensity, water status, and fertility levels without, however, any variance in genotype. The photographic illustrations and the following observations, measurements and comparisons describe plants grown in Lompoc, Calif., under commercial practice in a fiberglass-covered greenhouse with day temperatures about 21 to 24° C., night temperatures about 16 to 18° C. and light levels generally about 3,000 to 4,000 footcandles. Three rooted cuttings were planted in 20-cm hanging basket containers and grown for about 8 to 10 weeks.

In the following description, color references are made to The Royal Horticultural Society Colour Chart except where general terms of ordinary dictionary significance are used.

Botanical classification: *Impatiens walleriana* cultivar Cameo Salmon Chiffon.

Parentage:

*Male parent.*—Inventor's proprietary *Impatiens walleriana* selection code number W1, not patented.

*Female parent.*—Inventor's proprietary *Impatiens walleriana* selection code number 8713A, not patented.

Propagation:

*Type cutting.*—Terminal cuttings.

*Time to initiate roots.*—Summer: About 10 days with 21° C. Winter: About 12 days at 21° C.

*Time to produce a rooted cutting or liner.*—Summer and winter: About 28 days at 21° C.

*Root description.*—Numerous, fibrous, fine and freely branching.

Plant description:

*General appearance.*—Compact, mounded and spreading. Appropriate for 10 to 15-cm pots and 20 and 25-cm hanging basket containers.

*Growth and branching habit.*—Vigorous and freely-branching with at least ten lateral branches at the base, dense and bushy growth. Pinching, that is, removal of the terminal apices, is typically not required.

*Crop time.*—Rapid growth rate. From planting one rooted cutting in a 10-cm pot, not pinched: About 5 to 6 weeks. From planting three rooted cuttings in a 20-cm hanging basket container: Pinched, about 8 to 10 weeks; not pinched, about 6 to 8 weeks.

*Plant height.*—About 17 cm.

*Plant spread.*—About 30 cm.

*Lateral branches.*—Length: About 19 cm. Diameter: About 9 mm. Internode length: About 1 to 3 cm. Color: 146C; slight purplish anthocyanin on young stems.

*Foliage description.*—Leaves simple, alternate; broad and rounded, generally symmetrical; abundant, densely foliated. Length: About 3.75 cm. Width: About 2.75 cm. Shape: Ovate. Apex: Acute. Base: Rounded. Margin: Serrate. Texture: Glabrous. Color: Young foliage, upper surface: 146B. Young foliage, lower surface: 146C. Fully expanded foliage, upper surface: 146A. Fully expanded foliage, lower surface: 147C. Venation, upper surface: 146B. Venation, lower surface: 146B. Petiole: Length: About 1.2 to 1.5 cm. Diameter: About 2 mm. Color: 146B.

Flower description:

*Flower type and habit.*—Numerous and consistently double light and dark pink bi-colored flowers. Freely and continuously flowering. Flower buds open similar to a rose in fullness; flowers rounded. Flowers arise from leaf axils. Usually about 8 to 15 flowers and flower buds per lateral branch. Flowers positioned above the foliage and typically face outward to upward. Flowers last about 7 to 10 days on the plant depending on temperature and weather conditions. Flowers not persistent. Flowers not fragrant.

*Flowering season.*—Year-round under greenhouse conditions. In the garden, flowering is continuous from spring until fall.

*Flower size.*—Diameter: About 4.5 cm. Depth: About 2 cm.

*Flower buds.*—Rate of opening: From showing color to fully open flower, about 5 to 7 days is typical depending on temperature. Length: About 1.5 cm. Diameter: About 1 cm. Shape: Obovate.

*Petals.*—Quantity/arrangement: About 30 to 35 per flower; imbricate. Length: About 2.5 cm. Width: About 2 cm. Shape: Ovate or roughly cordate. Apex: Rounded or emarginate. Base: Acute. Margin: Entire. Texture: Smooth. Color: When opening, upper surface: 55C; stripes and speckles of 52D. When opening, lower surface: 52D. Fully opened, upper surface: 55C to lighter than 55C, close to 55D; stripes and speckles of 52D; fading to predominantly 55C with subsequent development. Fully opened, lower surface: 55C to 55D.

*Peduncles.*—Length: About 2.75 cm. Angle: About 45° to the lateral branch. Strength: Strong.

*Reproductive organs.*—None observed.

*Seed.*—Not observed.

Disease resistance: Plants of the new Impatiens have demonstrated good resistance to pathogens common to Impatiens, such as Botrytis.

It is claimed:

1. A new and distinct cultivar of Double Impatiens plant named 'Cameo Salmon Chiffon', as illustrated and described.

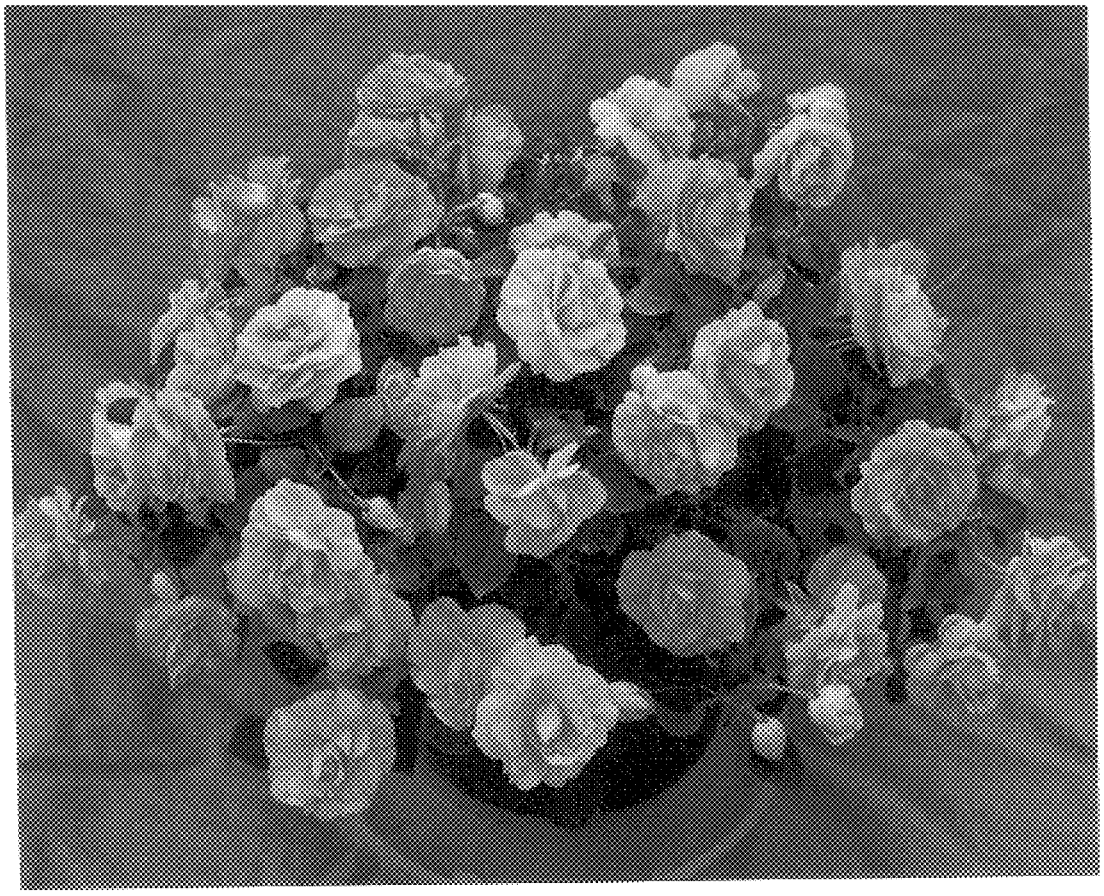

* * * * *